US006916554B2

(12) United States Patent  
Ma et al.

(10) Patent No.: US 6,916,554 B2  
(45) Date of Patent: Jul. 12, 2005

(54) ORGANIC LIGHT EMITTING MATERIALS AND DEVICES

(75) Inventors: Bin Ma, Monroeville, PA (US); Robert W. Walters, Export, PA (US); David B. Knowles, Apollo, PA (US); Raymond Kwong, Plainsboro, NJ (US); Yeh-Jiun Tung, West Windsor, NJ (US); Peter I. Djurovich, Long Beach, CA (US); Mark E. Thompson, Anaheim, CA (US)

(73) Assignees: The University of Southern California, Los Angeles, CA (US); Universal Display Corporation, Ewing, NJ (US)

( * ) Notice: Subject to any disclaimer, the term of this patent is extended or adjusted under 35 U.S.C. 154(b) by 53 days.

(21) Appl. No.: 10/288,785

(22) Filed: Nov. 6, 2002

(65) Prior Publication Data

US 2004/0086742 A1 May 6, 2004

(51) Int. Cl.⁷ .................... H05B 33/14; C09K 11/06; C07D 211/00
(52) U.S. Cl. ............. 428/690; 428/917; 313/504; 546/4
(58) Field of Search ............... 428/690, 917; 313/504; 257/40, 102; 252/301.16; 546/4

(56) References Cited

U.S. PATENT DOCUMENTS

| | | | |
|---|---|---|---|
| 4,769,292 A | 9/1988 | Tang et al. | 428/690 |
| 5,247,190 A | 9/1993 | Friend et al. | 257/40 |
| 5,703,436 A | 12/1997 | Forrest et al. | 313/506 |
| 5,707,745 A | 1/1998 | Forrest et al. | 428/432 |
| 5,834,893 A | 11/1998 | Bulovic et al. | 313/506 |
| 5,844,363 A | 12/1998 | Gu et al. | 313/506 |
| 6,013,982 A | 1/2000 | Thompson et al. | 313/506 |
| 6,087,196 A | 7/2000 | Sturm et al. | 438/29 |
| 6,091,195 A | 7/2000 | Forrest et al. | 313/504 |
| 6,097,147 A | 8/2000 | Baldo et al. | 313/506 |
| 6,294,398 B1 | 9/2001 | Kim et al. | 438/22 |
| 6,303,238 B1 | 10/2001 | Thompson et al. | 428/690 |
| 6,337,102 B1 | 1/2002 | Forrest et al. | 427/64 |
| 6,468,819 B1 | 10/2002 | Kim et al. | 438/22 |
| 2002/0024293 A1 | 2/2002 | Igarashi et al. | 313/504 |
| 2002/0028329 A1 | 3/2002 | Ise et al. | 428/336 |
| 2002/0064681 A1 | 5/2002 | Takiguchi et al. | 428/690 |
| 2002/0121638 A1 | 9/2002 | Grushin et al. | 257/40 |
| 2003/0059646 A1 * | 3/2003 | Kamatani et al. | 428/690 |
| 2003/0108771 A1 * | 6/2003 | Lecloux et al. | 428/690 |
| 2003/0230980 A1 | 12/2003 | Forrest et al. | 313/600 |
| 2004/0197602 A1 * | 10/2004 | Dobbs et al. | 428/690 |

FOREIGN PATENT DOCUMENTS

| | | |
|---|---|---|
| DE | 102 38 903 A1 | 3/2004 |
| EP | 1 191 613 | 3/2002 |
| WO | 02/02714 | 1/2002 |
| WO | 02/15645 | 2/2002 |
| WO | WO 02/45466 | 6/2002 |
| WO | WO 02/068435 A1 | 9/2002 |
| WO | WO 03/084972 A1 * | 10/2003 |

OTHER PUBLICATIONS

M. A. Baldo, et al., "Highly efficient phosphorescent emission from organic electroluminescent devices," Nature, Sep. 1998, vol. 395, pp. 151–154.
M.A. Baldo, et al., "Very high–efficiency green organic light–emitting devices based on electrophosphorescence", Applied Physics Letters, vol. 75, No. 1, pp. 4–6, Jul. 5, 1999.
C. Adachi, et al., "Nearly 100% internal phosphorescence efficiency in an organic light emitting device", J. Appl. Phys. 90, (Nov. 2001), pp. 5048–5051.
H. Zollinger, "Color Chemistry" VCH Publishers, 1991.
H, J, A, Dartnall, J. K. Bowmaker, and J. D. Mollon, Proc. Roy. Soc. B (London), 1983, 220, 115–130. (no month).
P.L. Coe et al., "The lithiation of fluorinated benzenes and its dependence on solvent and temperature", J. Chem. Soc. Perkin Trans. I, pp. 2729–2737, 1995. (no month).
A.J. Bridges et al., "A Dramatic Solvent Effect during Aromatic Halogen–Metal Exchanges. Different Products from Lithiation of Polyfluorobromobenzenes in Ether and THF", J. Org. Chem., vol. 55, pp. 773–775, Jan. 5, 1990.
Thomas H. Lowry et al., Mechanism and Theory in Organic Chemistry, Third Edition, New York, Harper & Row publishers, pp. 143–151, 1997.
N. Miyaura, et al., "Palladium–Catalyzed Cross–Coupling Reactions of Organoborn Compounds", Chem. Rev. 1995, vol. 95, No. 7, pp. 2457–2483, Nov. 1995.
D. Cuperly, et al., "First Direct C–2–Lithiation of 4–DMAP. Convenient Access to Reactive Functional Derivatives and Ligands", J. Org. Chem. 2002, vol. 67, No. 1, pp. 238–241, Jan. 11, 2002.
International Search Report to corresponding PCT application PCT/US03/25938, dated Dec. 22, 2003.

* cited by examiner

Primary Examiner—Marie Yamnitzky
(74) Attorney, Agent, or Firm—Kenyon & Kenyon

(57) ABSTRACT

An organic light emitting device is provided. The device has an anode, a cathode, and an emissive layer disposed between the anode and the cathode. The emissive layer further comprises an emissive material having the structure:

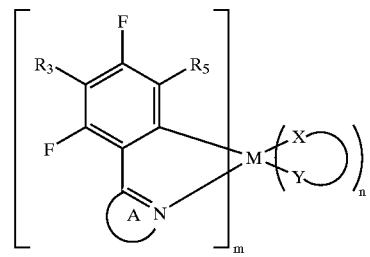

M may be a metal having an atomic weight greater than 40. $R_3$ may be a substituent having a Hammett value less than about –0.17, between about –0.15 and 0.05, or greater than about 0.07. $R_5$ may be H or any substituent. A may be a 5 or 6 member heteroaryl ring system. "m" may be at least 1. "n" may be at least zero. (X-Y) may be an ancillary ligand. The emissive material itself is also provided. The emissive material may have improved stability, and may provide a saturated blue emission.

26 Claims, 3 Drawing Sheets

ORGANIC LIGHT EMITTING MATERIALS AND DEVICES

RESEARCH AGREEMENTS

The claimed invention was made by, on behalf of, and/or in connection with one or more of the following parties to a joint university-corporation research agreement: Princeton University, The University of Southern California, and the Universal Display Corporation. The agreement was in effect on and before the date the claimed invention was made, and the claimed invention was made as a result of activities undertaken within the scope of the agreement.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

As used herein, the term "organic" includes polymeric materials as well as small molecule organic materials that may be used to fabricate organic optoelectronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be an fluorescent or phosphorescent small molecule emitter.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

OLED devices are generally (but not always) intended to emit light through at least one of the electrodes, and one or more transparent electrodes may be useful in an organic opto-electronic devices. For example, a transparent electrode material, such as indium tin oxide (ITO), may be used as the bottom electrode. A transparent top electrode, such as disclosed in U.S. Pat. Nos. 5,703,436 and 5,707,745, which are incorporated by reference in their entireties, may also be used. For a device intended to emit light only through the bottom electrode, the top electrode does not need to be transparent, and may be comprised of a thick and reflective metal layer having a high electrical conductivity. Similarly, for a device intended to emit light only through the top electrode, the bottom electrode may be opaque and/or reflective. Where an electrode does not need to be transparent, using a thicker layer may provide better conductivity, and using a reflective electrode may increase the amount of light emitted through the other electrode, by reflecting light back towards the transparent electrode. Fully transparent devices may also be fabricated, where both electrodes are transparent. Side emitting OLEDs may also be fabricated, and one or both electrodes may be opaque or reflective in such devices.

As used herein, "top" means furthest away from the substrate, while "bottom" means closest to the substrate. For example, for a device having two electrodes, the bottom electrode is the electrode closest to the substrate, and is generally the first electrode fabricated. The bottom electrode has two surfaces, a bottom surface closest to the substrate, and a top surface further away from the substrate. Where a first layer is described as "disposed over" a second layer, the first layer is disposed further away from substrate. There may be other layers between the first and second layer, unless it is specified that the first layer is "in physical contact with" the second layer. For example, a cathode may be described as "disposed over" an anode, even though there are various organic layers in between.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art. CIE coordinates are described in H. Zollinger, "Color Chemistyy" VCH Publishers, 1991 and H, J, A, Dartnall, J. K. Bowmaker, and J. D. Mollon, Proc. Roy. Soc. B (London), 1983, 220, 115-130, which are incorporated by reference.

For example, the NTSC standard calls for a saturated blue having CIE (0.155, 0.07). The SRGB standard calls for CIE (0.15, 0.06). Other industry standards may call for slightly different CIE coordinates.

SUMMARY OF THE INVENTION

An organic light emitting device is provided. The device has an anode, a cathode, and an emissive layer disposed between the anode and the cathode. The emissive layer further comprising an emissive material having the structure:

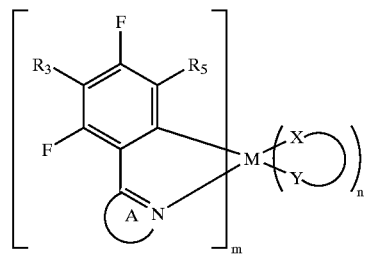

M may be a metal having an atomic weight greater than 40. $R_3$ may be a substituent having a Hammett value less than about −0.17, between about −0.15 and 0.05, or greater than about 0.07.

$R_5$ may be H or any substituent. A may be a 5 or 6 member heteroaryl ring system. "m" may be at least 1. "n" may be at least zero. (X-Y) may be an ancillary ligand. The emissive material itself is also provided. The emissive material may have improved stability, and may provide a saturated blue emission.

DETAILED DESCRIPTION

Figure 1:
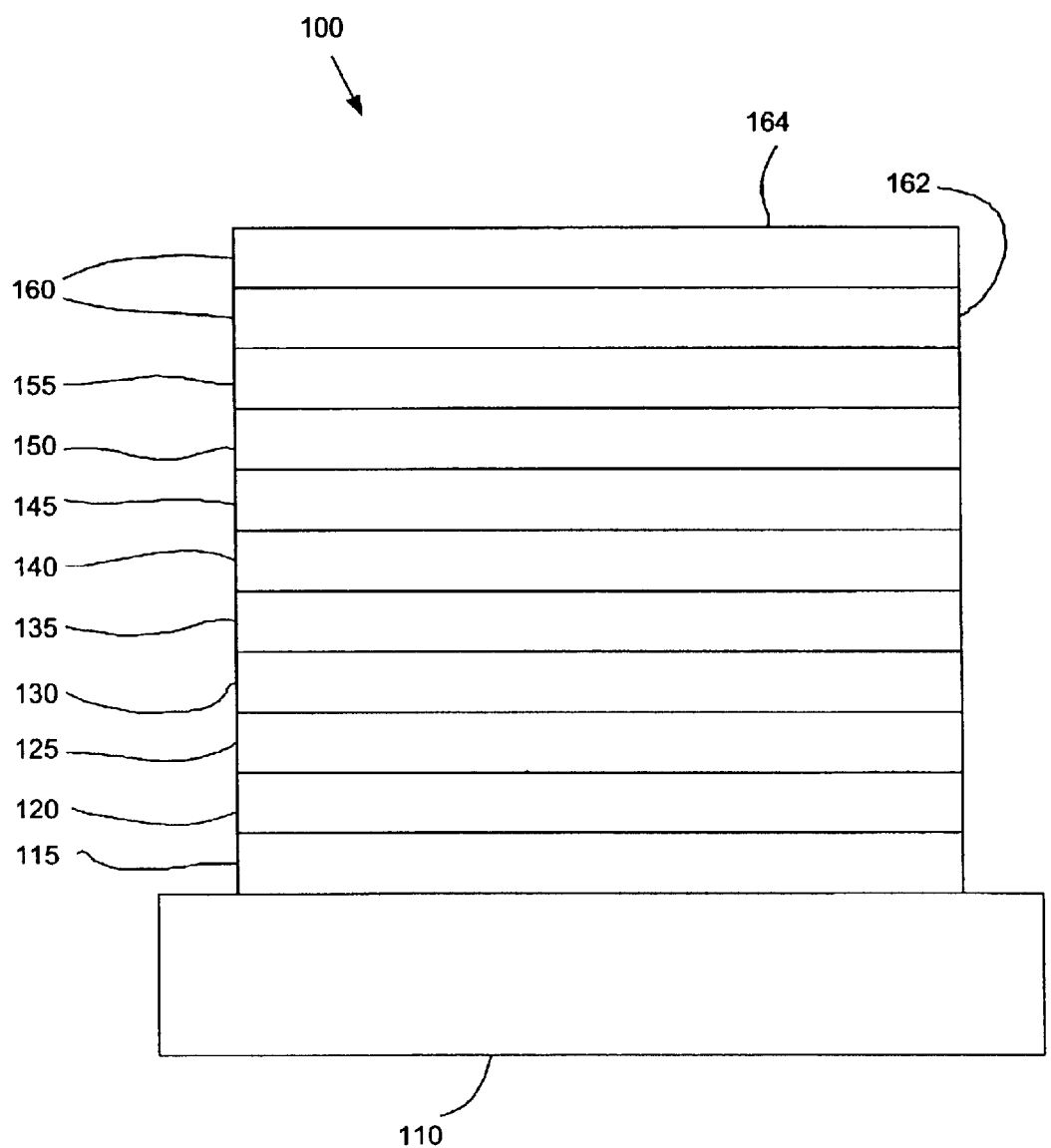
FIG. 1 shows an organic light emitting device having separate electron transport, hole transport, and emissive layers, as well as other layers.

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices", Nature, vol. 395, 151-154, 1998; ("Baldo-I") and Baldo et al., "Very high-efficiency green organic light-emitting devices based on electrophosphorescence", Appl. Phys. Lett., vol. 75, No. 3, 4-6 (1999) ("Baldo-II"), which are incorporated by reference in their entireties. Phosphorescence may be referred to as a "forbidden" transition because the transition requires a change in spin states, and quantum mechanics indicates that such a transition is not favored. As a result, phosphorescence generally occurs in a time frame exceeding at least 10 nanoseconds, and typically greater than 100 nanoseconds. If the natural radiative lifetime of phosphorescence is too long, triplets may decay by a non-radiative mechanism, such that no light is emitted. Organic phosphorescence is also often observed in molecules containing heteroatoms with unshared pairs of electrons at very low temperatures. 2,2'-bipyridine is such a molecule. Non-radiative decay mechanisms are typically temperature dependent, such that a material that exhibits phosphorescence at liquid nitrogen temperatures may not exhibit phosphorescence at room temperature. But, as demonstrated by Baldo, this problem may be addressed by selecting phosphorescent compounds that do phosphoresce at room temperature.

Generally, the excitons in an OLED are believed to be created in a ratio of about 3:1, i.e., approximately 75% triplets and 25% singlets. See, Adachi et al., "Nearly 100% Internal Phosphorescent Efficiency In An Organic Light Emitting Device," J. Appl. Phys., 90, 5048 (2001), which is incorporated by reference in its entirety. In many cases, singlet excitons may readily transfer their energy to triplet excited states via "intersystem crossing," whereas triplet excitons may not readily transfer their energy to singlet excited states. As a result, 100% internal quantum efficiency is theoretically possible with phosphorescent OLEDs. In a fluorescent device, the energy of triplet excitons is generally lost to radiationless decay processes that heat-up the device, resulting in much lower internal quantum efficiencies. OLEDs utilizing phosphorescent materials that emit from triplet excited states are disclosed, for example, in U.S. Pat. No. 6,303,238, which is incorporated by reference in its entirety.

Phosphorescence may be preceded by a transition from a triplet excited state to an intermediate non-triplet state from which the emissive decay occurs. For example, organic molecules coordinated to lanthanide elements often phosphoresce from excited states localized on the lanthanide metal. However, such materials do not phosphoresce directly from a triplet excited state but instead emit from an atomic excited state centered on the lanthanide metal ion. The europium diketonate complexes illustrate one group of these types of species.

Phosphorescence from triplets can be enhanced over fluorescence by confining, preferably through bonding, the organic molecule in close proximity to an atom of high atomic number. This phenomenon, called the heavy atom effect, is created by a mechanism known as spin-orbit coupling. Such a phosphorescent transition may be observed from an excited metal-to-ligand charge transfer (MLCT) state of an organometallic molecule such as tris(2-phenylpyridine)iridium(III).

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order.

Substrate 110 may be any suitable substrate that provides desired structural properties. Substrate 110 may be flexible or rigid. Substrate 110 may be transparent, translucent or opaque. Plastic and glass are examples of preferred rigid substrate materials. Plastic and metal foils are examples of preferred flexible substrate materials. Substrate 110 may be a semiconductor material in order to facilitate the fabrication of circuitry. For example, substrate 110 may be a silicon wafer upon which circuits are fabricated, capable of controlling OLEDs subsequently deposited on the substrate. Other substrates may be used. The material and thickness of substrate 110 may be chosen to obtain desired structural and optical properties.

Anode 115 may be any suitable anode that is sufficiently conductive to transport holes to the organic layers. The material of anode 115 preferably has a work function higher than about 4 eV (a "high work function material"). Preferred anode materials include conductive metal oxides, such as indium tin oxide (ITO) and indium zinc oxide (IZO), aluminum zinc oxide (AlZnO), and metals. Anode 115 (and substrate 110) may be sufficiently transparent to create a bottom-emitting device. A preferred transparent substrate and anode combination is commercially available ITO (anode) deposited on glass or plastic (substrate). A flexible and transparent substrate-anode combination is disclosed in U.S. Pat. No. 5,844,363, which is incorporated by reference in its entirety. Anode 115 may be opaque and/or reflective. A reflective anode 115 may be preferred for some top-emitting devices, to increase the amount of light emitted from the top of the device. The material and thickness of anode 115 may be chosen to obtain desired conductive and optical properties. Where anode 115 is transparent, there may be a range of thickness for a particular material that is thick enough to provide the desired conductivity, yet thin enough to provide the desired degree of transparency. Other anode materials and structures may be used.

Hole transport layer 125 may include a material capable of transporting holes. Hole transport layer 130 may be intrinsic (undoped), or doped. Doping may be used to enhance conductivity. α-NPD and TPD are examples of intrinsic hole transport layers. An example of a p-doped hole transport layer is m-MTDATA doped with $F_4$-TCNQ at a molar ratio of 50:1, as disclosed in United States Patent Application Publication No. 2003/0230980, which is incorporated by reference in its entirety. Other hole transport layers may be used.

Emissive layer 135 may include an organic material capable of emitting light when a current is passed between anode 115 and cathode 160. Preferably, emissive layer 135 contains a phosphorescent emissive material, although fluorescent emissive materials may also be used. Phosphorescent materials are preferred because of the higher luminescent efficiencies associated with such materials. Emissive layer 135 may also comprise a host material capable of transporting electrons and/or holes, doped with an emissive material that may trap electrons, holes, and/or excitons, such that excitons relax from the emissive material via a photoemissive mechanism. Emissive layer 135 may comprise a single material that combines transport and emissive properties. Whether the emissive material is a dopant or a major constituent, emissive layer 135 may comprise other materials, such as dopants that tune the emission of the emissive material. Emissive layer 135 may include a plurality of emissive materials capable of, in combination, emitting a desired spectrum of light. Examples of phosphorescent emissive materials include $Ir(ppy)_3$. Examples of fluorescent emissive materials include DCM and DMQA. Examples of host materials include $Alq_3$, CBP and mCP. Examples of emissive and host materials are disclosed in U.S. Pat. No. 6,303,238 to Thompson et al., which is incorporated by reference in its entirety. Emissive material may be included in emissive layer 135 in a number of ways. For example, an emissive small molecule may be incorporated into a polymer or dendrimer molecule. Other emissive layer materials and structures may be used.

Electron transport layer 140 may include a material capable of transporting electrons. Electron transport layer 140 may be intrinsic (undoped), or doped. Doping may be used to enhance conductivity. $Alq_3$ is an example of an intrinsic electron transport layer. An example of an n-doped electron transport layer is BPhen doped with Li at a molar ratio of 1:1, as disclosed in United States Patent Application Publication No. 2003/0230980, which is incorporated by reference in its entirety. Other electron transport layers may be used.

Cathode 160 may be any suitable material or combination of materials known to the art, such that cathode 160 is capable of conducting electrons and injecting them into the organic layers of device 100. Cathode 160 may be transparent or opaque, and may be reflective. Metals and metal oxides are examples of suitable cathode materials. Cathode 160 may be a single layer, or may have a compound structure. FIG. 1 shows a compound cathode 160 having a thin metal layer 162 and a thicker conductive metal oxide layer 164. In a compound cathode, preferred materials for the thicker layer 164 include ITO, IZO, and other materials known to the art. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The part of cathode 160 that is in contact with the underlying organic layer, whether it is a single layer cathode 160, the thin metal layer 162 of a compound cathode, or some other part, is preferably made of a material having a work function lower than about 4 eV (a "low work function material"). Other cathode materials and structures may be used.

Blocking layers may be used to reduce the number of charge carriers (electrons or holes) and/or excitons that leave the emissive layer. An electron blocking layer 130 may be disposed between emissive layer 135 and the hole transport layer 125, to block electrons from leaving emissive layer 135 in the direction of hole transport layer 125. Similarly, a hole blocking layer 140 may be disposed between emissive layer 135 and electron transport layer 145, to block holes from leaving emissive layer 135 in the direction of electron transport layer 140. Blocking layers may also be used to block excitons from diffusing out of the emissive layer. The theory and use of blocking layers is described in more detail in U.S. Pat. No. 6,097,147 and United States Patent Application Publication No. 2003/0230980, which are incorporated by reference in their entireties.

Generally, injection layers are comprised of a material that may improve the injection of charge carriers from one layer, such as an electrode or an organic layer, into an adjacent organic layer. Injection layers may also perform a charge transport function. In device 100, hole injection layer 120 maybe any layer that improves the injection of holes from anode 115 into hole transport layer 125. CuPc is an example of a material that may be used as a hole injection layer from an ITO anode 115, and other anodes. In device 100, electron injection layer 150 may be any layer that improves the injection of electrons into electron transport layer 145. LiF/Al is an example of a material that may be used as an electron injection layer into an electron transport layer from an adjacent layer. Other materials or combinations of materials may be used for injection layers. Depending upon the configuration of a particular device, injection layers may be disposed at locations different than those shown in device 100. More examples of injection layers are provided in U.S. patent application Ser. No. 09/931,948 to Lu et al., which is incorporated by reference in its entirety.

A protective layer may be used to protect underlying layers during subsequent fabrication processes. For example, the processes used to fabricate metal or metal oxide top electrodes may damage organic layers, and a protective layer may be used to reduce or eliminate such damage. In device 100, protective layer 155 may reduce damage to underlying organic layers during the fabrication of cathode 160. Preferably, a protective layer has a high carrier mobility for the type of carrier that it transports (electrons in device 100), such that it does not significantly increase the operating voltage of device 100. CuPc, BCP, and various metal phthalocyanines are examples of materials that may be used in protective layers. Other materials or combinations of materials may be used. The thickness of protective layer 155 is preferably thick enough that there is little or no damage to underlying layers due to fabrication processes that occur after organic protective layer 160 is deposited, yet not so thick as to significantly increase the operating voltage of device 100. Protective layer 155 may be doped to increase its conductivity. For example, a CuPc or BCP protective layer 160 may be doped with Li. A more detailed description of protective layers may be found in U.S. patent application Ser. No. 09/931,948 to Lu et al., which is incorporated by reference in its entirety.

Figure 2:
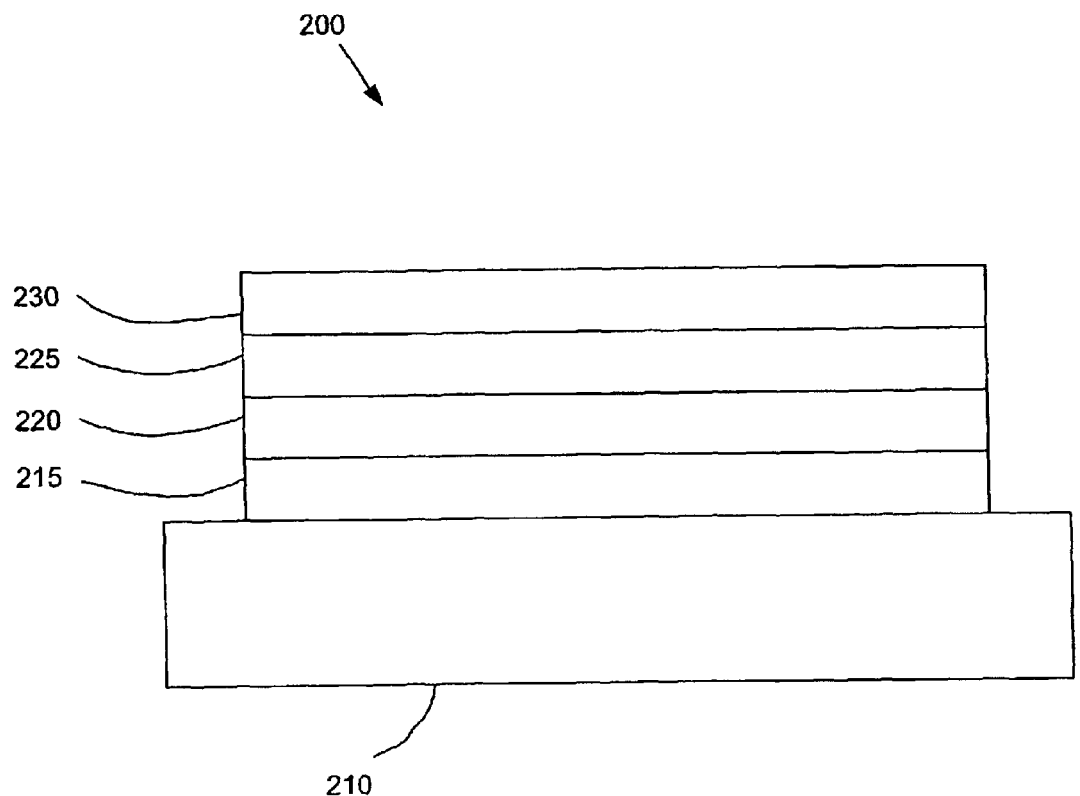
FIG. 2 shows an inverted organic light emitting device that does not have a separate electron transport layer.

FIG. 2 shows an inverted OLED 200. The device includes a substrate 210, an cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190, Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and /or a pit structure as described in U.S. Pat. No. 5,834,893 to Bulovic et al., which are incorporated by reference in their entireties.

Any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and organic vapor jet deposition (OVJD), such as described in U.S. patent application Ser. No. 10/233,470, which is incorporated by reference in its entirety. Other suitable deposition methods include spin coating and other solution based processes. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

Industry standards for full color displays call for a saturated red, green and blue emissive materials. "Saturated blue" means having a CIE coordinate of about 0.155, 0.07. However, a phosphorescent material more stable than FIrpic and having a CIE coordinate closer to saturated blue than FIrpic would be an improvement over presently available phosphorescent blue emitting materials. "Closer" to saturated blue means having CIE coordinates that are a smaller distance from 0.155, 0.07. For example, the distance between FIrpic (CIE 0.17, 0.32) and saturated blue is the square root of $((0.17-0.155)^2+(0.32-0.07)^2)$, or about 0.25044. So, a stable material having a distance less than about 0.25, and more preferably less than about 0.125, would be a desirable improvement. Another way to measure the color of emission is by peak wavelength. But, a peak wavelength measurement does not include certain useful information. For example, two different materials may emit spectra having the same peak wavelength, yet the emissions may appear different to the human eye because of the shape of the rest of the emission spectra. For example, two materials may have a peak wavelength of 470 nm. One material may have a sharp peak with very little tail into higher wavelengths, resulting in a saturated blue. The other material may have an extended tail into higher wavelengths, giving it an undesirable greenish tinge. CIE coordinates account for these differences.

"Stability" may be measured in a number of ways. One way is an $L_{100}/L_0$ test, which measures the photoluminescent emission of a thin film of material over time for at least 100 hours, and provides a parameter indicating what percentage of the original emission is still occurring at 100 hours. As used herein, $L_{100}/L_0$ means a stability test performed at about room temperature, under a vacuum of at least 1×10$^{-5}$ Torr or in an inert gas, and where the emissive material is incorporated into a film similar to one that might be used to make an organic light emitting device.

Many phosphorescent blue emitting materials generally have shortcomings, such as insufficient stability, or insufficient color saturation. One blue emitting phosphorescent material is FIrpic, which has the structure of Formula 1:

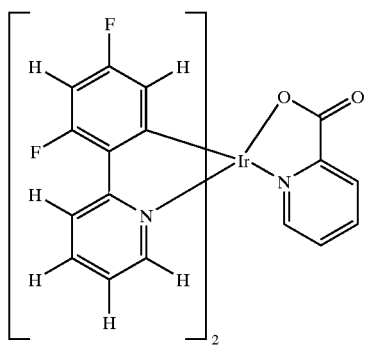

FIrpic in a non-polar solvent emits a photoluminescent spectrum at CIE 0.17, 0.32. FIrpic doped at 6% into CBP has an $L_{100}/L_0$ stability of 71% at an initial photoluminescent (PL) intensity of about 20 cd/M$^2$.

In one embodiment of the present invention, a method is provided for modifying FIrpic and similar materials based on metals other than Ir. The modification may increase stability and/or tune the color emitted by the material. The substituted molecule has the following structure of Formula 2:

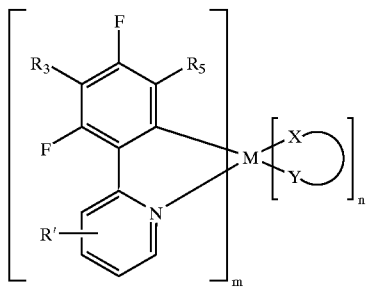

M may be any metal having an atomic weight greater than 40. Preferred metals include Ir, Pt, Pd, Rh, Re, Ru, Os, Tl, Pb, Bi, In, Sn, Sb, Te, Au, and Ag. More preferably, the metal is Ir or Pt. Most preferably, the metal is Ir.

$R_3$ may be any substituent, i.e., $R_3$ is not H. Preferably, any substituent other than $CH_3$ and F may be used. More preferably, the substituent may be selected from the group consisting of alkyl, alkoxy, amino, carboxy, cyano, aryls, and 5 and 6 member heteroaryls. Aryls include phenyl and napthyl. Heteroaryls include pyridine, pyrimidine and pyridazine. Any of these substituents may be further substituted. The relatively low stability of FIrpic is believed to be due in part to the two fluorine atoms on the phenyl ring. It has be documented that fluorine exerts the strongest acidifying effect between all of the halogens on an aromatic ring and specifically influences the acidifying effect at the ortho positions. When the fluorine groups are in a 1,3 relationship, hydrogen abstraction occurs in between at the two position. See Coe, P. L. et al, *J. Chem. Soc. Perkin Trans.* 1, 1995 pp. 2729-2737 and Bridges, A. J.; *J. Org. Chem,* 1990, 55 773-775. In the molecule FIrpic the same acidifying effect is observed, that is the hydrogen atom in the 3 position (between the two fluorines illustrated below as $R_3$) can be readily removed leading to instability. By substituting this hydrogen atom with a group that is less easily removed, the stability problem may be mitigated.

In a preferred embodiment, $R_3$ may be a group in which the atom connected to the phenyl ring possesses a non-empty p-orbital or n-orbital that may be in pi-conjugation or partial π-conjugation with the it-system in the phenyl ring. It is believed that such an $R_3$ substituent leads to enhanced stability. One example of such a substituent has a carbon in the $R_3$ substituent bound to the carbon in the 3 position, where the carbon in the $R_3$ substituent is bound to at least one other atom with at least a double bond, or is part of a resonating structure such as a phenyl ring. The double bond or resonating structure alters the orbital structure such that there is π-conjugation or partial π-conjugation with the n-system in the phenyl ring and the carbon in the substituent to which it is bound. Cyano and phenyl substituents provide examples of such a bonding arrangement. Another example of such a substituent is one having a lone pair of electrons, such as an oxygen atom or a nitrogen atom.

$R_5$ may be H or any substituent. Where a blue-emitting material is desired, preferred substituents for the $R_5$ position electron withdrawing groups. The substituents may be further substituted.

R' may be H or any substituent. R' may represent substitution at any number of sites on the pyridyl ring, including mono-, di-, tri-, and tetra-substitution. Where there is more than one substituent, multiple substituents may be linked to each other. Where a blue emitting material is desired, preferred substituents include electron donating groups. Examples of electron donating groups (when attached to the carbon para to the nitrogen) include methyl, methoxy, amino, dialkylamino, and 5 or 6 member cyclic amino groups such as morpholino, pyrrolidino, piperidino. Whether a group is electron donating or electron withdrawing may depend upon the position to which it is attached.

The (X-Y) ring may be referred to as an "ancillary ligand." (X-Y) may be any mono-anionic ligand. The ligand is referred to as "ancillary" because it is believed that it may modify the photoactive properties of the material, as opposed to directly contributing to the photoactive properties. By way of contrast, the ligand to the left is referred to as "photoactive" because it is believed that it contributes to the photoactive properties of the material. Although Formula 2 illustrates a bidentate ancillary ligand, other structures may be used. The definitions of photoactive and ancillary are intended as non-limiting theories.

"m" is the number of photoactive ligands of a particular type, and "n" is the number of ancillary ligands of a particular type. Depending upon the metal M, a certain number of ligands may be attached to the metal. Generally, the ligands are bidentate, which means that they form two bonds with the metal; but bidentate ligands are not required. For example, two chlorines could be attached to the metal in place of a bidentate ancillary ligand. "m" is at least one, and may be any integer greater than zero up to the maximum number of ligands that may be attached to the metal. "n" may be zero, and may be an integer greater than zero, subject to the requirement that "m" is at least one. "m"+"n" may be less than the total number of ligands that may be attached to M, such that ligands other than those specifically illustrated in Formula 2 may also be attached to M. These additional ligands may be photoactive or ancillary. For iridium, to which 3 bidentate ligands may be attached, "m" may be 1, 2 or 3, and "n" may be 0, 1 or 2.

The photoactive ligand has the structure of Formula 3:

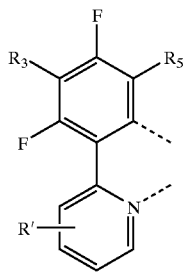

Preferred ancillary ligands include acetylacetonate (acac), picolinate (pic) and dipivaloylmetanate (t-butyl acac). Some preferred ancillary ligands have the following structure according to Formula 4 (pic), Formula 5 (acac), and Formula 6 (t-butyl acac). Other ancillary ligands may be used. Further non-limiting examples of ancillary ligands may be found in PCT Application Publication WO 02/15645 A1 to Lamansky et al. at pages 89-90, which are incorporated herein by reference:

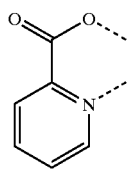  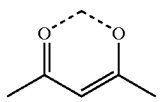  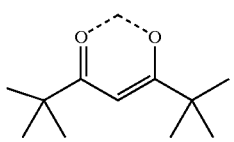

Picolinate        Acetylacetonate        dipivaloylmethanate

In a preferred embodiment, n is zero, and m is the maximum number of ligands that may be attached to the metal. For example, for Ir, m is three in this preferred embodiment, and the structure may be referred to as a "tris" structure. The tris structure is preferred because it is believed to be particularly stable. The stability of the tris structure, combined with the stability and color tuning provided by the $R_3$ group, may result in a particularly stable blue emitting phosphorescent material.

In one embodiment, m+n is equal to the total number of bidentate ligands that may be attached to the metal in question—for example, 3 for Ir. In another embodiment, m+n may be less than the maximum number of bidentate ligands that may be attached to the metal, in which case other ligands—ancillary, photoactive, or otherwise—may also be attached to the metal. Preferably, if there are different photoactive ligands attached to the metal, each photoactive ligand has the structure indicated in Formula 3.

In addition to enhancing stability, the $R_3$ substituent group may be used to tune the color of light emitted by the material. It is believed that an $R_3$ substituent having a negative Hammett value may red-shift the color emission, while an $R_3$ substituent having a positive Hammnett value may blue-shift the color of emission. The Hammett value of a group is a measure of whether it withdraws electrons (positive Hammett value), or donates electrons (negative Hammett value). The Hammett equation is described in more detail in: Thomas H. Lowry and Kathleen Schueller Richardson "Mechanism and Theory In Organic Chemistry," New York, 1987, pages 143-151, which is incorporated by reference. Where red-shifting is desired, a Hammett value less than −0.18 is preferred. Where blue-shifting is desired, the Hammett value is preferably greater than about 0.07, more preferably greater than about 0.2, and most preferably greater than about 0.6. These larger Hammett values are particularly desirable when a blue-emitting phosphorescent material is sought. A Hammett value having a smaller absolute value may not have a significant shifting effect. Where enhanced stability without color shifting is desired—for example, if a material already emits a desired spectra, such as saturated green—a Hammett value between about −0.16 and 0.5 is preferred. There are circumstances within the scope of the present invention where Hammett values outside of the ranges described may be appropriate.

Substituents in the $R_5$ and R' positions may also be used to tune the color emitted by the material. It is believed that the color-shifting effect of a substituent having a particular Hammett value may vary depending upon where the substituent is attached. For example, it is believed that a substituent attached to any position on the same phenyl ring as $R_3$ in FIrpic may cause a shift in the same direction—positive Hammett values correspond to blue shifting, and negative Hammett values to red shifting. But, a substituent attached to any position on the pyridyl ring may cause a shift in the opposite direction—positive Hammett values correspond to red shifting, and negative Hammett values correspond to blue shifting. Notably, the sign (and magnitude) of the Hammett value of a particular substituent may change depending upon where it is attached. The Hammett values associated with a "para" position, $\sigma_{para}$, are used for $R_3$, because $R_3$ is in the para position to the carbon coordinated to the metal.

Preferred substituents for the $R_3$ position include Ph, cyano, 4-$CF_3$Ph, and pyridine. It is believed that each of these substituents enhance stability. Each of these substituents except Ph also provides a blue shift relative to FIrpic. Ph provides a very mild red-shift, and may be useful for situations where enhanced stability without a significant color shift is desired.

A particularly preferred substituent for the $R_3$ position is a cyano group. It is believed that the cyano group advantageously provides enhanced stability, as well as a significant blue shift of about 15 nm from the unsubstituted analog. A substituted material having a photoactive ligand similar to FIrpic, with a cyano group in the 3 position, has the following structure of Formula 7. $R_5$ and R' may be H or a substituent, selected based on considerations similar to those discussed with respect to Formula 2. Formula 7:

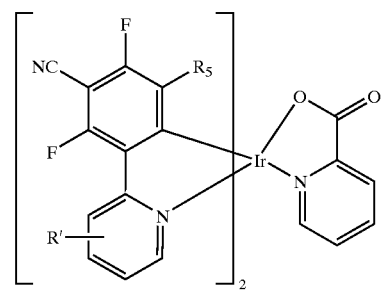

Various embodiments of the present invention may be applied to a class of materials more general than FIrpic derivatives. For example, in one embodiment of the present invention, substitutions may be made to the following material to enhance stability and/or tune color emission, in accordance with Formula 8:

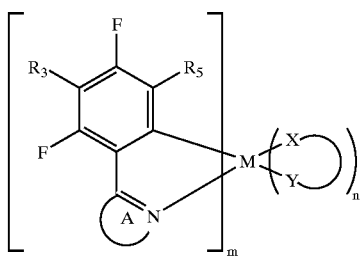

R₃ may be selected from the same substituents described with respect to Formula 2, for similar reasons. Phenyl and cyano groups are preferred R₃ substituents. CH₃ and F may also be used as a substituent in the R₃ position for materials where the bottom ring is not a 6-member pyridyl ring. The bottom ring "A" may be a heteroaryl ring system with at least one nitrogen atom that is coordinated to the metal M. Preferably, A is a 5 or 6 member heteroaryl ring system. A single or multiple additional heteroatoms, such as nitrogen or other heteroatoms, may also be incorporated. The heteroaryl ring may be benzanullated to yield various heteroaryl ring systems, such as quinoline, isoquinoline, and others. The ring may be substituted or unsubstituted in one or multiple positions. For example, such substituents may include alkyl, halogen, alkoxy, aryl, and/or heteroaryl. R₅ may be selected from the same substituents described with respect to Formula 2, for similar reasons.

In one embodiment of the invention, a stable phosphorescent material that emits a saturated blue is sought. In other embodiments, other colors are sought. For example, a saturated green or a saturated red may be obtained. While green and red phosphorescent materials are generally more available in the prior art than blue, embodiments of the present invention may lead to phosphorescent materials having better color saturation, better stability, or both.

Formula 2 is a preferred embodiment of the structure of Formula 8.

It is understood that the various embodiments described herein are by way of example only, and are not intended to limit the scope of the invention. For example, many of the materials and structures described herein may be substituted with other materials and structures without deviating from the spirit of the invention. It is understood that various theories as to why the invention works are not intended to be limiting. For example, theories relating to charge transfer are not intended to be limiting.

Material Definitions:

As used herein, abbreviations refer to materials as follows:
CBP: 4,4'-N,N-dicarbazole-biphenyl
m-MTDATA 4,4',4"-tris(3-methylphenylphenlyamino) triphenylamine
Alq₃: 8-tris-hydroxyquinoline aluminum
BPhen: 4,7-diphenyl-1, 10-phenanthroline
n-BPhen: n-doped BPhen (doped with lithium)
F₄-TCNQ: tetrafluoro-tetracyano-quinodimethane
p-MTDATA: p-doped m-MTDATA (doped with F4-TCNQ)
Ir(ppy)₃: tris(2-phenylpyridine)-iridium
Ir(PPZ)₃: tris(1-phenylpyrazoloto,N,C(2')iridium(M)
BCP: 2,9-dimethyl-4,7-diphenyl-1,0-phenanthroline
TAZ: 3-phenyl-4-(1'-naphthyl)-5-phenyl-1,2,4-triazole
CuPc: copper phthalocyanine.
ITO: indium tin oxide
NPD: naphthyl-phenyl-diamine
TPD: N,N'-bis(3-methylphenyl)N,N'-bis-(phenyl)-benzidine
BAlq: aluminum(III)bis(2-methyl-8-quinolinato)4-phenylphenolate
mCP: 1,3-N—N-dicarbazole-benzene
DCM: 4-(dicyanomethylene)-6-4-dimethylaminostyryl-2-methyl)-4H-pyran
DMQA: N,N'-dimethylquinacridone Experimental:

Specific representative embodiments of the invention will now be described, including how such embodiments may be made. It is understood that the specific methods, materials, conditions, process parameters, apparatus and the like do not necessarily limit the scope of the invention.

In Reaction A shown below, a compound represented by graphic formula III is prepared by combining the starting reagents represented by formulae I and II. The substituted or unsubstituted phenylboronic acids represented by graphic formula I may be purchased commercially or prepared using standard techniques as described by the following review; Chem. Rev. 1995, 95, 2457-2483, which also summarizes the palladium catalyzed cross-coupling reactions between organic halides and boronic acids. Compounds represented by graphic formula II, may also be purchased commercially or prepared by methods described in J. Org. Chem. 2002, 67, 238-241. In Reaction A compounds represented by graphic formula I are reacted with the appropriately substituted 2-chloro, bromo, or iodo pyridines represented by graphic formula II and are combined in an appropriate solvent, e.g. dimethoxyethane (DME), xylenes. In addition, an aqueous base solution e.g., Na₂CO₃, K₂CO₃, K₃PO₄, a palladium catalyst such as Pd(II) acetate, Pd(PPh₃)₄ and a reducing agent triphenylphosphine (TPP) if necessary is combined and refluxed until the reaction is completed. After purification using column chromatography, moderate to high yields are obtained to give III.

Reaction A

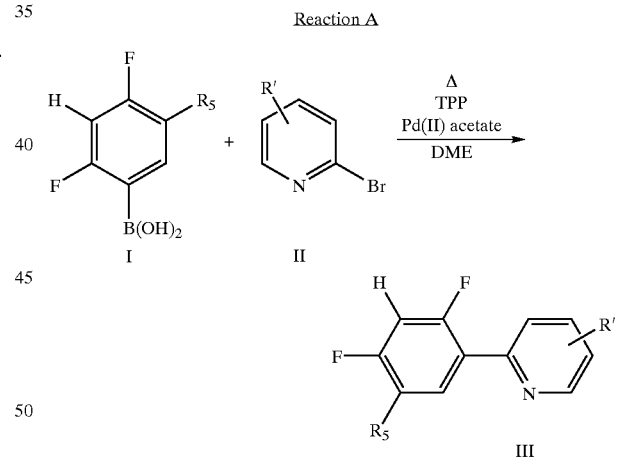

An alternate route to the desired substituted ligands (III) is shown in Reaction C and described in J. Org. Chem. 2002, 67, 238-241.

In reaction C compounds represented by graphic formula IV where the X substituent is any halogen can be prepared or are commercially available, the heteroaromatic stannanes represented by graphic formula V can be prepared using following the methods described in J. Org. Chem. 2002, 67, 238-241 and depicted in Reaction B (shown below). In Reaction B, a substituted pyridine is added to a mixture of N-dimethylethanolamine (DMEA) and butyl lithium at low temperatures. This is followed by the slow addition of the appropriate electrophile, (E⁺) i.e. tributyl tin chloride, bromine, carbon tetrabromide etc. The crude products are purified using standard techniques such as column chromatography and recrystallization and can be used in Reaction A or Reaction C.

Reaction B

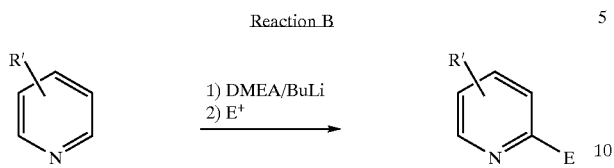

Compounds represented by graphic formulae IV and V shown below in Reaction C are combined in a solvent, e.g., xylenes, pyridine, toluene and reacted in the presence of a Palladium (II) or Palladium (0) catalyst e.g., $PdCl_2(PPh_3)_2$, $Pd(PPh_3)_4$ and a reducing agent, $PPh_3$ if needed to give the desired ligand represented by graphic formula III. Purification of the crude ligand III is performed using standard techniques such as column chromatography or precipitation using common solvents.

Reaction C

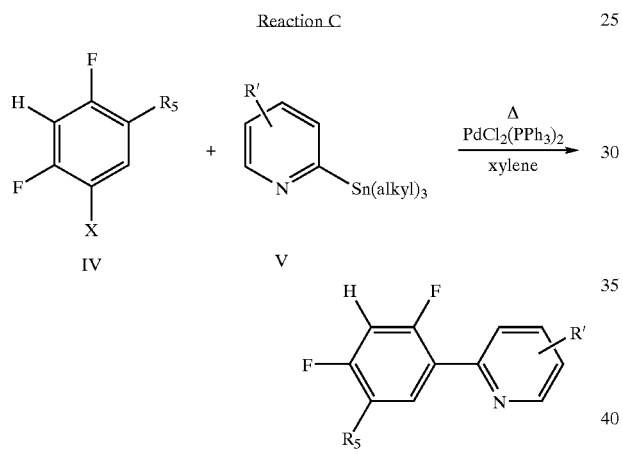

In reaction D below, a substituted or unsubstituted ligands are dissolved in anhydrous solvent i.e. THF to which a base i.e. LDA, is added at low temperatures. After addition of the base, an electrophile i.e, heptafluorobenzyl iodide is added. After the reaction is complete the crude material can be purified by standard conditions such as a silica gel to give the desired product represented by graphic formula VI. Compound VI is then reacted with the appropriate aryl or heteroaryl boronic acid in a similar manner described above in Reaction A to give compound VII.

Reaction D

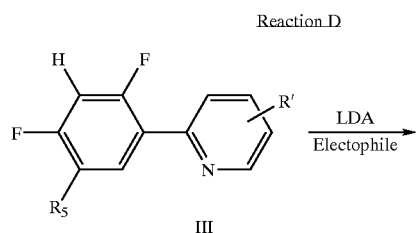

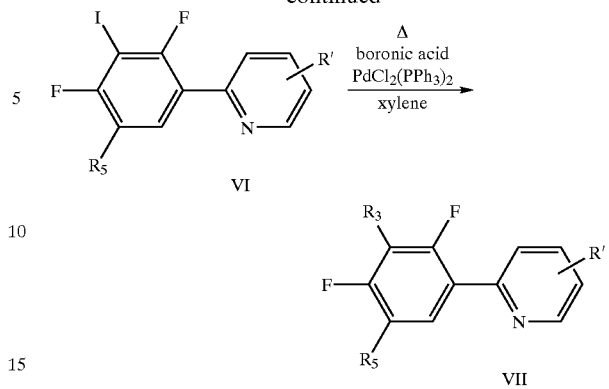

Alternatively, in Reaction E shown below, one could prepare compounds represented by graphic formula VII where $R_3$ is a cyano group by the following method. A compound represented by graphic formula VIII shown in Reaction E below is reacted at low temperatures with an appropriate base such as lithium diisopropyl amide (LDA) and quenched with carbon dioxide ($CO_2$). Compound IX is reacted with thionyl chloride and ammonium hydroxide to give X as the carboxamide. Compound X is then reacted under dehydrating conditions i.e. acid ($H^+$) to give XI. The compound represented by graphic formula XI is then converted to the photoactive ligand by replacing XI for IV in Reaction C to give III where $R_3$ is now substituted with a cyano substituent.

Reaction E

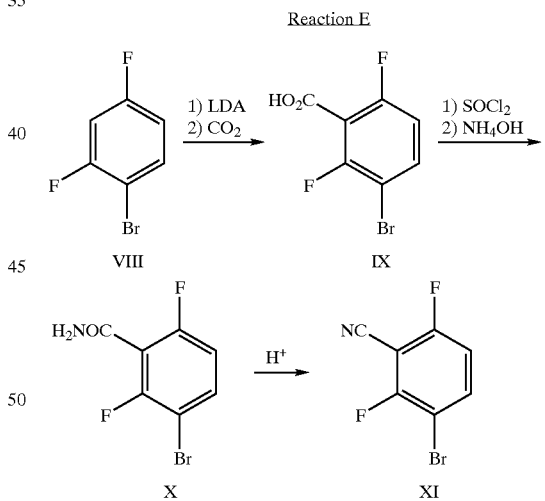

In Reaction F, the substituted or unsubstituted photoactive ligands prepared from Reaction D represented by graphic formula VII, can be reacted with a variety of metals, e.g., iridium, platinum, in the presence of a solvent, e.g., 2-methoxyethanol or 2-ethoxyethanol and water under refluxing conditions to produce the dichloro-bridge dimer represented by graphic formula XII. A solid precipitate that is formed upon completion of the reaction is collected by vacuum filtration techniques and further purified if necessary.

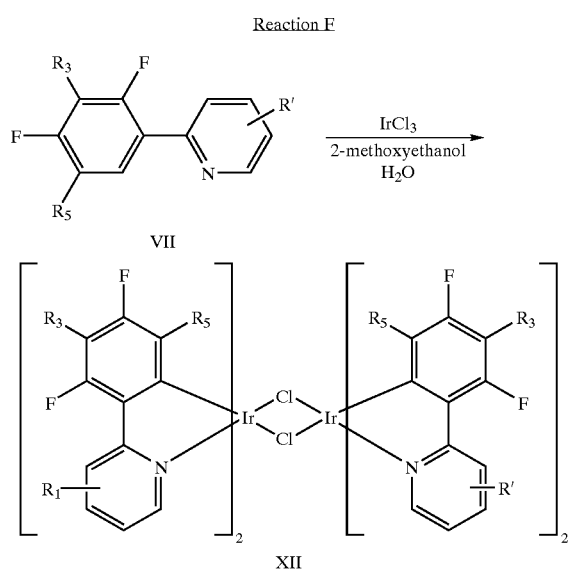

Reaction F

VII

XII

In Reaction G the dichloro-bridge dimers represented by graphic formula XII can be reacted with a variety of mono-anionic coordinating ligands, e.g. acetonacetyl (acac), picolinic acid, 4-dimethylaminopicolinic acid (DMAPic) and is denoted by X and Y. The final isolated products represented by graphic XIII are purified by standard techniques.

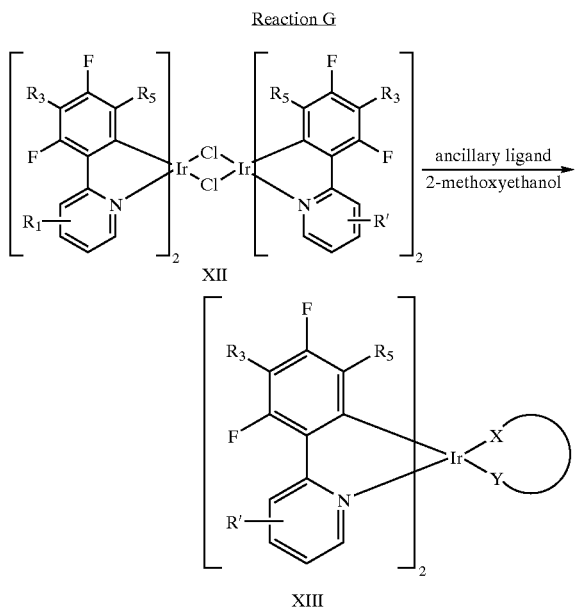

Reaction G

XII

XIII

Each of the materials in Table 1 was synthesized. Each material had the structure illustrated by Formula 2, where M=Ir, and $R_5$=R'=H. Except for entry 11, each of the materials had m=2, with one ancillary ligand (n=1) as indicated. Entry 11 had m=3, as indicated by the "tris" entry in the ancillary column, such that there was no ancillary ligand. Entries 1 and 3 were synthesized in accordance with the examples provided above. The other entries were synthesized using similar techniques apparent to one of skill in the art in view of the examples provided above. A small amount of each material was dissolved in dichloromethane. Each solution was optically pumped, and the resultant photoluminescent spectra were measured. The resultant peak wavelengths and CIE coordinates are tabulated in Table 1. Hammett values for the R3 substituent in the para position ($\sigma_{para}$) were drawn from the literature for compound 1 ($\sigma_{para}$ for Ph=−0.01), and compounds 10 and 11 ($\sigma_{para}$ for CN=0.66).

TABLE 1

| Compound | $R_3$ | ancillary ligand | peak emission (nm) | PL CIE |
|---|---|---|---|---|
| 1 | Ph | pic | 474 | 0.17, 0.38 |
| 2 | 4-CF$_3$Ph | pic | 470 | 0.16, 0.33 |
| 3 | 2-pyridine | acac | 482 | 0.17, 0.45 |
| 4 | 2-pyridine | pic | 468 | 0.17, 0.34 |
| 5 | 2-pyrimidine | acac | 484 | 0.18, 0.46 |
| 6 | 2-pyrimidine | pic | 467 | 0.17, 0.33 |
| 7 | 4-pyridine | acac | 480 | 0.15, 0.39 |
| 8 | 4-pyridine | pic | 468 | 0.17, 0.33 |
| 9 | 3-pyridine | pic | 470 | 0.17, 0.33 |
| 10 | CN | pic | 452 | 0.15, 0.19 |
| 11 | CN | none (tris) | 450 | 0.17, 0.19 |
| 12 (FIrpic) | H | pic | 468 | 0.17, 0.32 |

Compounds 1 and 10 from Table 1, and FIrpic were further characterized for stability. The photoluminescent stability (PL) testing system used to test these samples monitors PL emission of a sample under UV excitation as a function of time. The system uses a mercury-xenon (Hg-Xe) UV lamp to excite a thin film sample on a quartz substrate. The broad UV emission of the lamp is delivered to the sample through a narrow band UV filter, which selects the 313 nm Hg line. During testing, the sample is kept under high vacuum (<5×10$^7$ Torr). Silicon diode photodetectors monitor the emission intensities of the thin film sample and the lamp.

Host and dopant were coevaporated in a vacuum chamber (<5×10$^{-8}$ Torr) from different sources to form a thin film of 50 nm thickness on a quartz substrate. The dopant was present in a concentration of 6 wt %. The host deposition rate was 1.6Π/s. Next, the sample was exposed to atmospheric pressure in an inert nitrogen ambient (<1 ppm O$_2$ and H$_2$O), where the sample was placed in the PL testing system vacuum chamber and subsequently evacuated to <1×10$^{-6}$ Torr. Next, the sample was exposed to 313 nm LW radiation at a power density of 0.6 mW/Cm$^2$, resulting in a PL intensity of at least 20 cd/m$^2$, and its photoluminescence intensity was recorded as a function of time. Also, the UV source intensity was recorded as a function of time.

Figure 3:
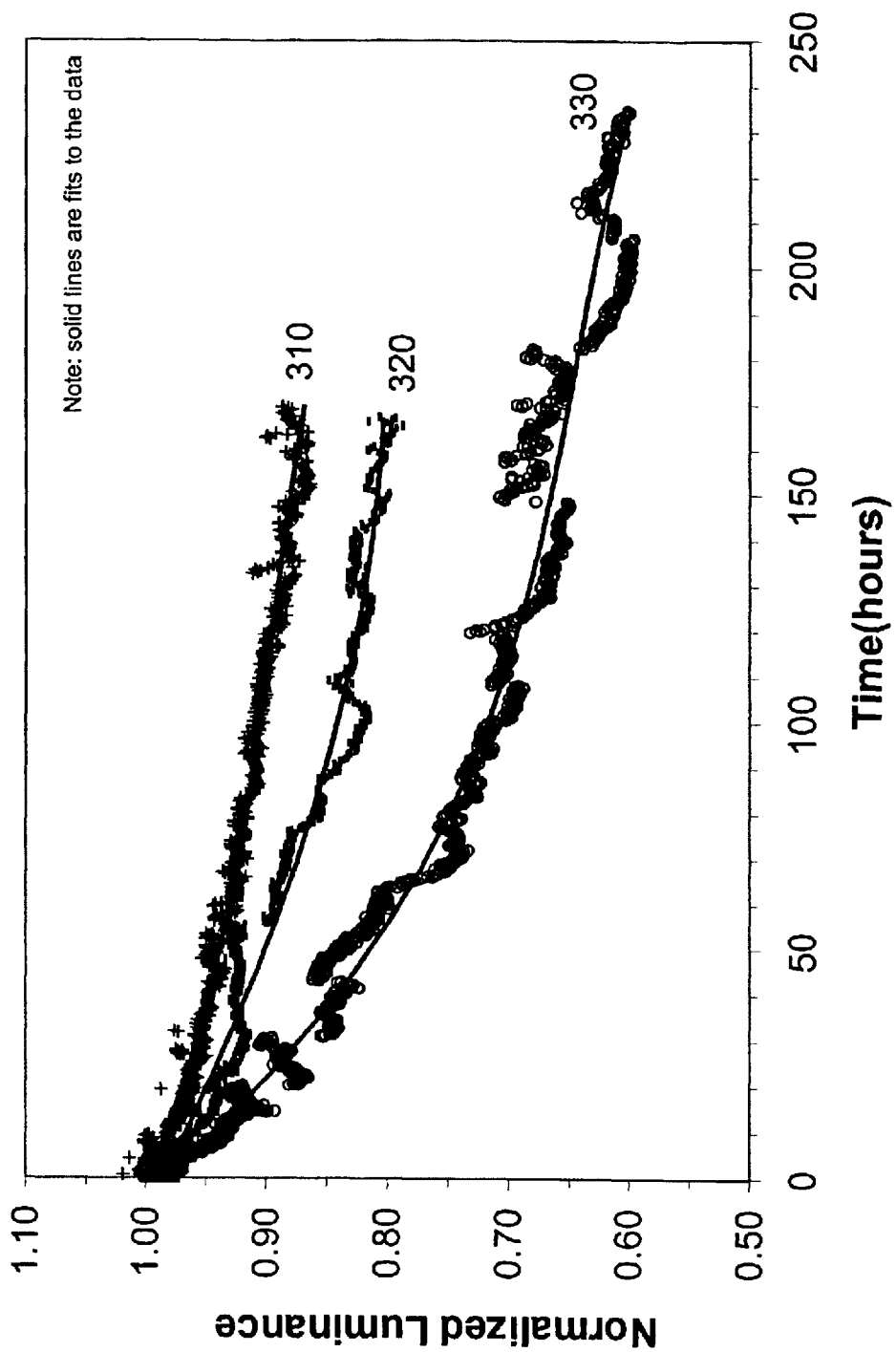
FIG. 3 shows stability plots for various materials.

Three samples were prepared. Sample 1 was Compound 1 doped into CBP. Sample 2 was compound 10 doped into mCP. Sample 3 was FIrpic doped into CBP. The host materials were selected based on energy transfer considerations, and it is not expected that the differences in host material will significantly affect photoluminescent lifetime testing results. Each thin film was optically pumped, and the photoluminescent intensity was measured as a function of time. The initial PL intensity was about 20 cd/m$^2$. The results are plotted in FIG. 3. Plots 310, 320 and 330 show the photoluminescent intensities of the compound 1, compound 10, and FIrpic films, respectively. $L_{100}/L_0$ values, which indicate the intensity at 100 hours as a percentage of the intensity at zero hours, were also determined for each material. The $L_{100}/L_0$ values for compound 1, compound 10, and FIrpic were 91%, 82% and 71%, respectively. The plots of FIG. 3, as well as the $L_{100}/L_0$ values, demonstrate that compound 1 and compound 10 are more stable than FIrpic, and demonstrate the more general principal that providing a substituent in the R3 position increases stability. These results show that some embodiments of the present invention have emission characteristics similar to FIrpic, or even closer to saturated blue than FIrpic, and with enhanced stability. Notably, compound 10 has a CE "distance" of about 0.120104 from saturated blue.

While the present invention is described with respect to particular examples and preferred embodiments, it is understood that the present invention is not limited to these examples and embodiments. The present invention as claimed therefore includes variations from the particular examples and preferred embodiments described herein, as will be apparent to one of skill in the art.

What is claimed is:

1. An emissive material having the structure:

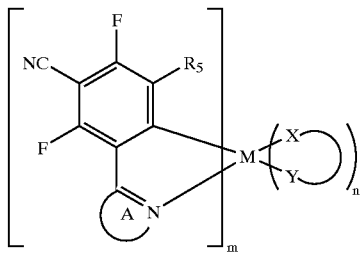

wherein:
M is a metal having an atomic weight greater than 40;
$R_5$ is H or any substituent;
A is a 5 or 6 member heteroaryl ring system;
m is at least 1;
n is at least zero;
(X-Y) is an ancillary ligand.

2. The emissive material of claim 1, wherein the emissive material has the structure:

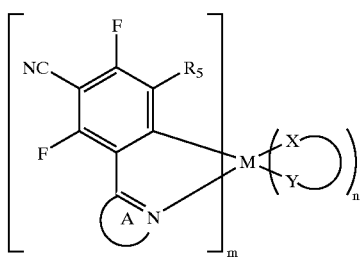

wherein R' is selected from the group consisting of H and any substituent, including mono-, di-, tri-, and tetra-substitution.

3. The emissive material of claim 2, wherein n is zero and m is the maximum number of bidentate ligands that may be attached to the metal M.

4. The emissive material of claim 2, wherein M is selected from the group consisting of Ir, Pt, Pd, Rh, Re, Ru, Os, Tl, Pb, Bi, In, Sn, Sb, Te, Au, and Ag.

5. The emissive material of claim 4, wherein M is Ir.

6. The emissive material of claim 5, wherein the emissive material has a photoluminescent $L_{100}/L_0$ stability of at least 82%.

7. The emissive material of claim 6, wherein the emissive material has a photoluminescent $L_{100}/L_0$ stability of at least 91%.

8. The emissive material of claim 6, wherein the emissive material in a non-polar solvent has CIE coordinates within a radius of 0.25 from saturated blue.

9. The emissive material of claim 6, wherein the emissive material in a non-polar solvent has CIE coordinates within a radius of 0.125 from saturated blue.

10. The emissive material of claim 6, wherein the emissive material in a non-polar solvent emits a spectrum having a peak wavelength of 452 nm or less.

11. The emissive material of claim 5, wherein at least one of $R_5$ and R' is selected from the group consisting of electron withdrawing groups and electron donating groups.

12. The emissive material of claim 5, wherein m is 3, n is zero, and R' and $R_5$ are unsubstituted.

13. The emissive material of claim 4, wherein M is Pt.

14. The emissive material of claim 2, wherein n is zero.

15. The emissive material of claim 2, wherein the emissive material has the structure:

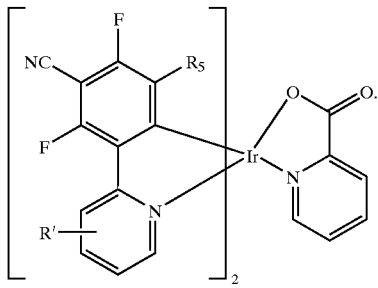

16. The emissive material of claim 15, wherein $R_5$ and R' are unsubstituted.

17. The emissive material of claim 1, wherein A is a substituted heteroaryl ring system.

18. The emissive material of claim 1, wherein the material is dispersed in a polymer or dendrimer.

19. The emissive material of claim 1, wherein the material is consists of a polymer or dendrimer.

20. An emissive material comprising a ligand having the structure:

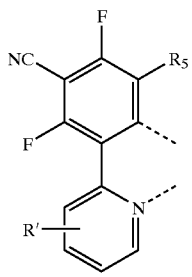

wherein:
the ligand is attached to a metal having an atomic weight greater than 40;
$R_5$ is H or any substituent; and
wherein R' is selected from the group consisting of H and any substituent, including mono-, di-, tri-, and tetra-substitution.

21. An organic light emitting device, comprising:
(a) an anode;
(b) a cathode; and
(c) an emissive layer disposed between the anode and the cathode, wherein the emissive layer comprises an emissive material having the structure:

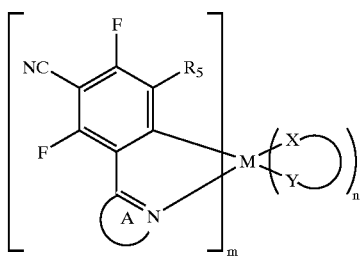

wherein:

M is a metal having an atomic weight greater than 40;

$R_5$ is H or any substituent;

A is a 5 or 6 member heteroaryl ring system;

m is at least 1;

n is at least zero;

(X-Y) is an ancillary ligand.

22. The device of claim 21, wherein the emissive material has the structure:

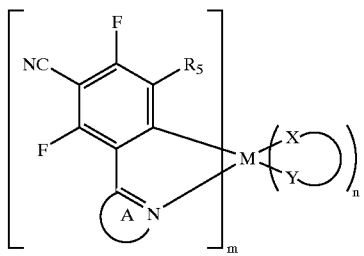

wherein R' is selected from the group consisting of H and any substituent, including mono-, di-, tri-, and tetra-substitution.

23. The device of claim 22, wherein the emissive material has the structure:

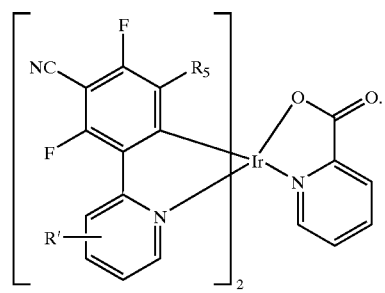

24. The device of claim 23, wherein $R_5$ and R' are unsubstituted.

25. The device of claim 22, wherein m is 3, n is zero, and R' and $R_5$ are unsubstituted.

26. An organic light emitting device, comprising:
(a) an anode;
(b) a cathode; and
(c) an emissive layer disposed between the anode and the cathode, wherein the emissive layer comprises an emissive material comprising a ligand having the structure:

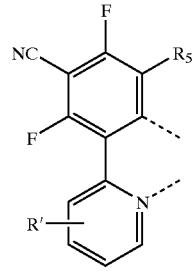

wherein:
the ligand is attached to a metal having an atomic weight greater than 40;
$R_5$ is H or any substituent; and
wherein R' is selected from the group consisting of H and any substituent, including mono-, di-, tri-, and tetra-substitution.

* * * * *

UNITED STATES PATENT AND TRADEMARK OFFICE
CERTIFICATE OF CORRECTION

PATENT NO. : 6,916,554 B2
DATED : July 12, 2005
INVENTOR(S) : Ma et al.

It is certified that error appears in the above-identified patent and that said Letters Patent is hereby corrected as shown below:

Column 2,
Line 32, change "chemistyy" to -- chemistry --.

Column 6,
Line 20, change "layerl" to -- layer --.

Column 11,
Line 56, change "Hammnett" to -- Hammett --.

Column 14,
Line 58, change "In reaction C" to -- In reaction C, --.
Line 64, change "N-diethylethanolamine" to -- N,N-diethylethanolamine --.

Column 19,
Lines 37-47, delete the following structure
"
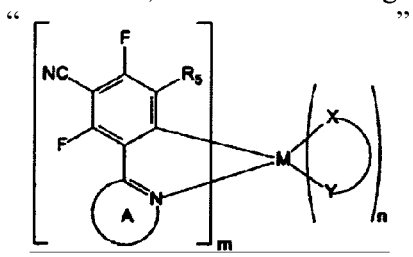
"
and insert the following structure
--
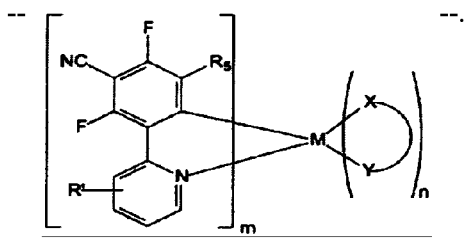
--.

UNITED STATES PATENT AND TRADEMARK OFFICE
CERTIFICATE OF CORRECTION

PATENT NO. : 6,916,554 B2
DATED : July 12, 2005
INVENTOR(S) : Ma et al.

It is certified that error appears in the above-identified patent and that said Letters Patent is hereby corrected as shown below:

Column 21,
Lines 27-37, delete the following structure
"
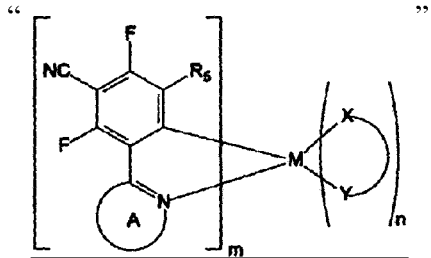
"
and insert the following structure
--
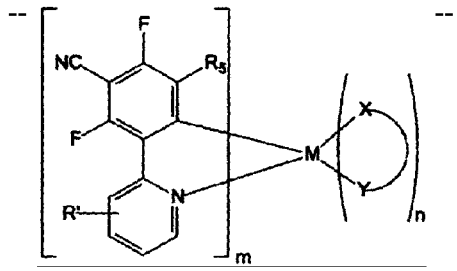
--

Signed and Sealed this

Sixteenth Day of May, 2006

JON W. DUDAS
*Director of the United States Patent and Trademark Office*